United States Patent [19]

Levy et al.

[11] Patent Number: 5,538,856
[45] Date of Patent: * Jul. 23, 1996

[54] SCREENING KIT AND METHOD FOR DIAGNOSING CHRONIC IMMUNE DYSFUNCTION SYNDROME

[75] Inventors: Jay A. Levy, San Francisco, Calif.; Alan L. Landay, Oak Park, Ill.

[73] Assignee: The Regents of the University of California, Oakland, Calif.

[*] Notice: The term of this patent shall not extend beyond the expiration date of Pat. No. 5,426,028.

[21] Appl. No.: 399,774

[22] Filed: Mar. 7, 1995

Related U.S. Application Data

[62] Division of Ser. No. 787,389, Nov. 4, 1991, Pat. No. 5,426,028, which is a continuation of Ser. No. 725,309, Jul. 5, 1991, abandoned.

[51] Int. Cl.⁶ .................................................. G01N 33/577
[52] U.S. Cl. ............................ 435/7.24; 435/5; 435/975; 436/548
[58] Field of Search .............................. 435/5, 7.24, 975; 436/548

[56] References Cited

U.S. PATENT DOCUMENTS 5,426,028  6/1995  Levy et al. ............................ 435/7.24

OTHER PUBLICATIONS

M. Lopez et al, Biol. Abstr. 80, Abstr. No. 41755, 1985.
Holmes et al., "Chronic Fatigue Syndrome: A Working Case Definition", *Annales of Internal Medicine*, 108:387–389 (1988).
Straus et al., "Persisting Illness and Fatigue in Adults with Evidence of Epstein–Barr Virus Infection", *Annales of Internal Medicine*, 102:7–16 (1985).
Tobi et al., "Prolonged Atypical Illness Associated with Serological Evidence of Persistent Epstein–Barr Virus Infection", *Lancet*, 1:61–64 (1982).
Krueger et al., "Antibody Prevalence to HBLV (Human Herpesvirus–6, HHV–6) and Suggestive Pathogenicity in the General Population and in Patients with Immune Deficiency Syndromes", *Journal of Virological Methods*, 21:125–131 (1988).
Wakefield et al., "Human Herpesvirus 6 and Myalgic Encephalomyelitis", *Lancet*, 1:1059 (1988).
Yousef et al., "Chronic Enterovirus Infection in Patients with Postviral Fatigue Syndrome", *Lancet*, 1:146 (1988).
Miller et al., "Antibody to Coxsackie B Virus in Diagnosing Postviral Fatigue Syndrome", *British Journal of Medicine*, 302:140–143 (1991).
Palca, J., "Does a Retrovirus Explain Fatigue Syndrome Puzzle?", *Science*, 249:1240–1241 (1990).
DeFrietas et al., "Retro Viral Sequences Related to Human T–Lymphotropic Virus Type II in Patients with Chromic Fatigue Immune Dysfunction Syndrome", *Proceedings of the National Academy of Sciences (USA)*, 88:2922–2926 (1991).

Kibler et al., "Immune Function in Chronic Active Epstein–Barr Virus Infection", *Journal of Clinical Immunology*, 5:46–54 (1985).
Tosato et al., "Characteristic T Cell Dysfunction in Patients with Chronic Active Epstein–Barr Virus Infection (Chronic Infectious Mononucleosis)", *Journal of Immunology*, 5:3082–3088 (1985).
Caligiuri et al., "Phenotypic and Functional Deficiency of Natural Killer Cells in Patients with Chronic Fatigue Syndrome", *Journal of Immunology*, 10:3306–3313 (1987).
Klimas et al., "Immunologic Abnormalities in Chronic Fatigue Syndrome", *Journal of Clinical Microbiology*, 6:1403–1410 (1990).
Rouse et al., "Immunosuppression in Viral Infections", *Reviews of Infectious Diseases*, 8:850–873 (1986).
Buchwald et al., "Frequency of 'Chronic Active Epstein–Barr Virus Infection' in a General Medical Practice", *Journal of the American Medical Association*, 257:2303–2307 (1987).
Levy et al., "Frequent Isolation of HHV–6 from Saliva and High Seroprevalence of the Virus in the Population", *Lancet*, 335:1047–1050 (1990).
Archard, "Postviral fatigue syndrome: persistance of enterovirus RNA in muscle and elevated creatine kinase", *Journal of the Royal Society for Medicine*, 81:326–9 (1988).
Lloyd et al., "Immunological Abnormalities in the Chronic Fatigue Syndrome", *Medical Journal of Australia*, 151:122 (1989).
Gin et al., "Immune Function and the Chronic Fatigue Syndrome", *Medical Journal of Australia*, 151:117–119 (1989).
Notkins et al., "Effect of Virus Infections on the Function of the Immune System", *Annual Review of Microbiology*, 24:525 (1970).

*Primary Examiner*—David Saunders
*Attorney, Agent, or Firm*—Karl Bozicevic; Fish & Richardson

[57] ABSTRACT

The subject invention permits diagnosis of chronic fatigue syndrome (CFS) by analyzing peripheral blood mononuclear cell subset populations and activation markers. A positive diagnosis for CFS is associated with an increase in the percentage of CD8+ cells showing CD38 or HLA-DR cell markers or a decrease in CD11b markers in CD8+ cells. The analysis is preferably performed using fluorochrome-labelled monoclonal antibodies specific for a determinant of the above subset cells and activation markers.

5 Claims, 1 Drawing Sheet

SCREENING KIT AND METHOD FOR DIAGNOSING CHRONIC IMMUNE DYSFUNCTION SYNDROME

CROSS-REFERENCES

This application is a divisional application of earlier filed U.S. patent application Ser. No. 07/787,389, filed Nov. 4, 1991 issued U.S. Pat. No. 5,426,028, which is a continuation application of earlier filed application Ser. No. 07/725,309, filed Jul. 5, 1991 (now abandoned) to which applications we claim priority under 35 USC §120 and which applications are incorporated herein by reference in their entirety.

TECHNICAL FIELD

The invention concerns methods for diagnosing chronic fatigue syndrome as well as cell cultures containing an infectious agent associated with chronic fatigue syndrome.

BACKGROUND

Chronic fatigue syndrome (CFS) is being reported with increasing frequency in many sections of the United States as well as other parts of the world, including England and Australia. In many patients, CFS begins with an acute "flu-like" illness and is characterized by a debilitating fatigue lasting for more than 3–6 months; chronic and recurrent low-grade fever, pharyngitis, adenopathy, myalgia, arthralgia, sleep disorders and mood disorders. A common feature is multilevel brain disorder, reflected in mental changes such as loss of memory, vertigo, and disorientation, often described as "spaciness." Direct measurements of brain function using, for example, magnetic resonance imaging (MRI) have indicated abnormalities in the central nervous system. Dementia and signs of "mental clouding" have also been documented through psychoneurologic testing.

The infectious agent(s) for CFS is unknown; the agent is suspected to be viral, at least in part because many viral infections are characterized by chronic fatigue. However, post viral fatigue generally does not persist for more than a few weeks, which is contrary to the clinical picture in CFS. Conclusive evidence of an etiologic association of a particular known virus to CFS has not been presented, although high levels of antibodies to Epstein Barr virus (EBV), human herpes virus-6 (HHV-6) and the p24 core antigen of HTLV have been reported. Further, certain immunologic abnormalities described in CFS are often found in viral infections, including activation of CD8+ cells. Other immunologic abnormalities observed include decreased function of NK cells, reduced mitogenic responses of lymphocytes and B-cell subset changes.

It is of interest to determine whether there are virologic and immunologic parameters which are at least substantially specific for CFS so that they can be used as a diagnostic aid in those patients who present with symptoms including chronic fatigue. Further, definitive diagnosis of CFS is hampered by the lack of a screening test such as an immune profile or a serologic test to identify the etiologic agent. Identification of the etiologic agent to produce recombinant proteins that are safe for use in vaccines, diagnostics, and/or screening of the blood supply is greatly desired.

Relevant Literature

The Centers for Disease Control (CDC) have attempted to define CFS in recent cases using major and minor criteria. Holmes et al., *Ann. Intern. Med.* (1988) 108:387–89. CFS has been reported to be associated with Epstein-Barr virus. See, Strauss et al. *Ann. Intern. Med.* (1985) 102:7–16; Buchwald et al. *JAMA* (1987) 257:2303–7; and Tobi et al., *Lancet* (1982) 1:61–4. High antibody levels to HHV-6 observed in some CFS patients also do not correlate with any particular symptoms nor with virus isolation. See, for example, Levy et al., *The Lancet* (1990) 335:1047–50; Krueger et al., *J. Virol. Methods* (1988) 21:125; and Wakefield et al., *The Lancet* (1988) 1:1059. The presence of enteroviral antigens in muscles of people with CFS has been reported, and Coxsackie virus infections are reported to be associated with fatigue. Archard et al., *J. Royal Soc. Med.* (1988) 81:326–9; and Yousef et al., *Lancet* (1988) 1:146–50. However, an association of Coxsackie virus with CFS has not been confirmed. Miller, *BMJ* (1991) 302:140. Likewise, the linking of an HTLV-like virus with CFS, while suggested, has not been confirmed. Palca, *Science* (1990) 249:1240–41; DeFrietas et al., *PNAS* (May, 1991).

Decreased function of NK cells, reduced mitogenic response of lymphocytes, B-cell subset changes, and activation of CD8+ cells with CFS have been reported. Kibler et al., *J. Clin. Immunol.* (1985) 5:46–54; Tosato et al., *J. Immunol.* (1985) 134:3082–88; Murdoch Nv. *Ned. J.* (1988) 101:511–2; Caligiuri et al., *J. Immunol.* (1987) 139:3306–13; Lloyd et al., *Med. J. Australia* (1989) 151:122–24; Jin et al, *Med. J. Aust.* (1989) 151:117–19; and Klimas et al., *J. Clin. Micro.* (1990) 28:1403–10. Infected animals and patients suffering or recovering from a variety of acute viral infections frequently display transient immune abnormalities and chronic fatigue. Notkins et al., *Ann. Rev. Microbiol.* (1970) 24:525; Rouse and Horchov, *Rev. Insect. Dis.* (1986) 8:850–73.

SUMMARY OF THE INVENTION

In accordance with the subject invention, methods are provided for diagnosing chronic fatigue syndrome in a host presenting symptoms which include chronic fatigue. The method involves the step of screening peripheral blood mononuclear cells (PMC) from a host for changes in PMC markers as compared to PMC from a healthy control. Also provided are cell culture procedures for finding the infectious agent associated with CFS. The cell cultures can be used as a source of genomic material for preparing polynucleotide probes for diagnosis of CFS, as well as antigens and vaccines for therapeutic and diagnostic applications. Propagation of the infectious agent in vitro can be used to identify cell surface antigens associated with the infectious agent and as a source of such antigens.

DESCRIPTION OF THE SPECIFIC EMBODIMENTS

Figure 1:
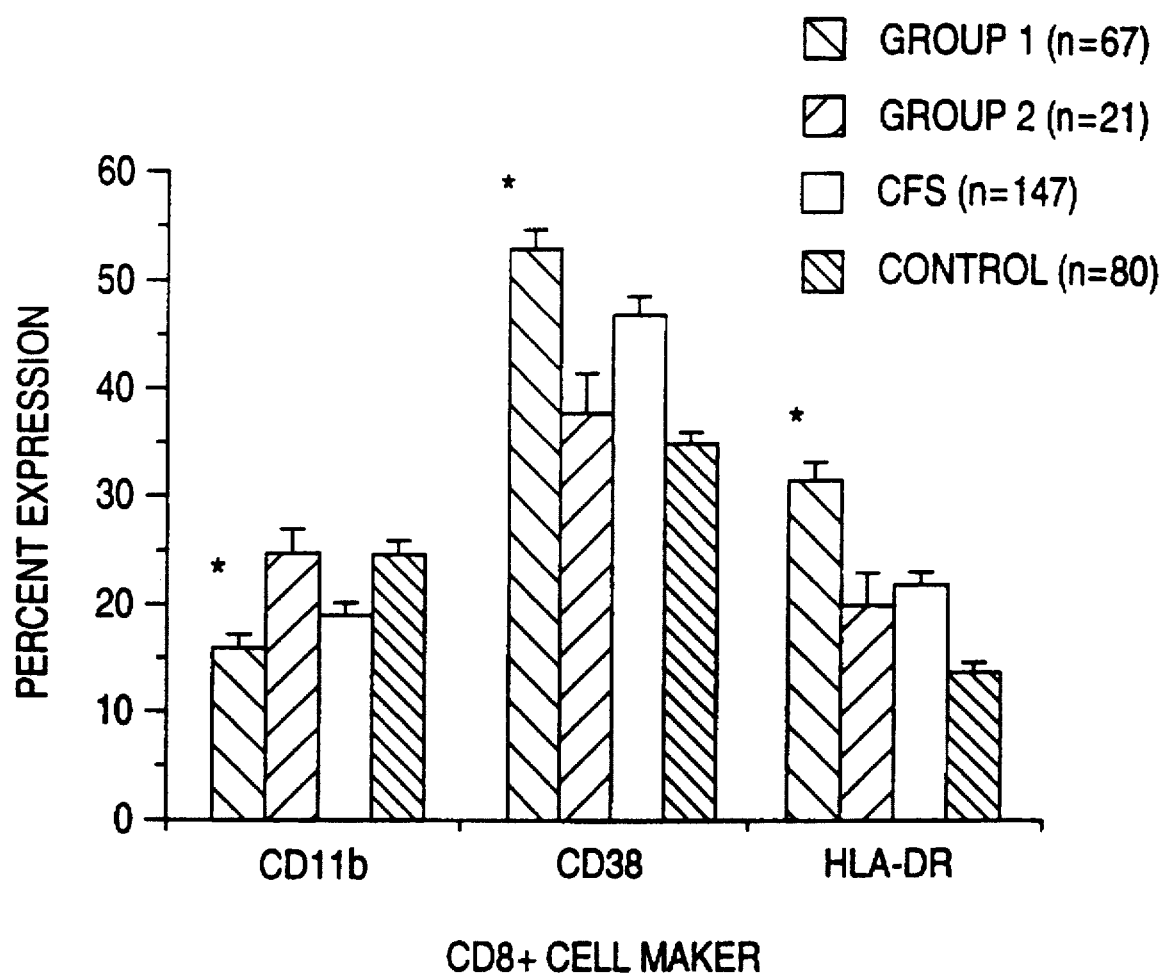
FIGURE 1 shows the percent expression (mean±standard error) of CD11b, CD38 and HLA-DR on CD8+ cells from normals, severely afflicted (group 1), recovering (group 2) and all CFS patients. *$p<0.05$ for group 1 patients with CFS as compared to control (Mann-Whitney U Test).

The present invention provides methods for diagnosing CFS, together with cell culture procedures for identifying the infectious agent associated with CFS. The method for diagnosing CFS involves use of an immunologic profile at least substantially specific for CFS as compared to the immunologic profile observed with other conditions such as depression, autoimmunity, and fatigue. To obtain the immunologic profile, peripheral blood mononuclear cell (PMC) subset populations and markers are evaluated for changes relative to those subset populations and markers found on PMC obtained from a host having symptoms of chronic fatigue syndrome. The changes associated with a diagnosis of CFS include a reduction in CD11b+ cells; an increase in CD11b− cells; and an increase in the percentage of CD8+ cells giving CD38+ and HLA-DR+ markers. All of these individual markers are significant ($p<0.01$) indicators of CFS compared to control populations. Patients with at least 2 of the 3 abnormal markers have >90% chance of having CFS.

The following symptoms are associated with chronic fatigue syndrome. Previously, in order to receive a preliminary diagnosis of CSF, a patient needed to fulfill major criteria 1 and 2 and the following minor criteria: (1) 6 or more of the 11 symptom criteria and 2 or more of the 3 physical criteria or (2) 8 or more of the 11 symptom criteria.

Major Criteria

1. New onset of persistent or relapsing, debilitating fatigue in a person with no previous history of similar symptoms: fatigue that does not resolve with bed rest and is severe enough to produce or impair average daily activity for a period of at least 6 months.
2. Other clinical conditions that may produce similar symptoms must be excluded by thorough evaluation, based on history, physical examination, and laboratory findings.

Minor Criteria

Symptom criteria—began at or after onset of fatigue; must have persisted or recurred over a period of at least 6 months.

1. Mild fever—oral temperature between 37.5° and 38.6° C., if measured by the patient—or chills.
2. Sore throat.
3. Painful lymph nodes in the anterior or posterior cervical or axillary distribution.
4. Unexplained generalized muscle weakness.
5. Muscle discomfort or myalgia.
6. Prolonged (24 hours or greater) generalized fatigue after levels of exercise that would have been easily tolerated in the patient's premorbid state.
7. Generalized headaches different from ones the patient may have had in the premorbid state.
8. Migratory arthralgia without joint swelling or redness.
9. Neuropsychologic complaints (e.g. photophobia, transient visual scotomata, forgetfulness, excessive irritability, confusion, difficulty thinking, inability to concentrate, depression).
10. Sleep disturbance (hypersomnia or insomnia).
11. Description of the main symptom complex as initially developing over a few hours to a few days.

Physical Criteria

1. Low-grade fever.
2. Nonexudative pharyngitis.
3. Palpable or tender anterior or posterior cervical or axillary lymph nodes.

*Summarized from Holmes, et al. Ann Intern Med (1988) 108:387–9.

The present invention greatly simplifies and makes more definite a diagnosis of CFS. The method of the invention for diagnosing CFS involves developing a peripheral white blood cell profile of the host (patient) suspected of having CFS. The profile includes identification of the numbers and types of cells present in a PMC sample obtained from the host as well as an evaluation of the percentage of cells expressing activation antigens. The profile is then analyzed to determine if any abnormal level (which can be either an increase or a decrease, depending on the specific marker) of a particular PMC cell subset or marker can be found in comparison to PMC from a healthy control. The profile obtained with PMC from a host having symptoms of CFS as compared to PMC from a host not showing symptoms of CFS (control) is normalized by sample size or similar criterion which will allow meaningful comparison of the profiles obtained for different samples. Conveniently this may be accomplished by presenting the cell population of a given type in units of cells per sample volume, and the relative proportion of such cells as a percentage.

As is typical of diagnostic techniques, a range of differences from the mean value of any specific component of the profile is to be expected. Patents with mild symptoms are expected to exhibit only slight differences for any of the individual parameters while patents with severe symptoms are expected to exhibit greater differences. However, as with any diagnostic assay, different results can occur in patients who do not respond in the normal fashion of the general population, so that slight differences can occur in patients with severe symptoms and vice versa. Any of the normal statistical evaluation methods used to determine the significance of a single value from a mean can be used to evaluate the significance of a given difference. For example, values that fall outside one standard deviation from the mean have about a 90% chance of being statistically different from the mean. Since a range of mean±one standard deviation would still classify as abnormal relatively large portion of the general population, values more than two, preferably at least three, more preferably at least four, standard deviations from the mean are generally used to evaluate whether a single value (such as percentage of CD8+ cells) is outside the normal range and thus indicative of abnormality (i.e., CFS). However, it should be recognized that the present invention involves testing for the indicated results and any statistically significant difference and not necessarily finding such differences, since it is probable that a large number of individuals test for CFS will be found not to have CFS.

The subset cell profile can be obtained by any of a variety of methods including flow cytometry (FACS); see, for example, Levy et al., *Clin. Immunol. Immunopathol.* (1985) 35:328. In the FACS method of analysis, monoclonal antibodies to a variety of subset cells bind to and identify phenotypic antigens present on immune system cells. Commercially available antibodies exist that can detect the presence of these markers, so that preparation of the antibodies is not required. One supplier of these (and other) antibodies is Becton Dickinson Immunocytometry Systems of Mountain View, Calif. Other antibodies which identify the same or a closely linked antigenic marker would be expected to give similar diagnostic results. Thus, where a marker antigen is designated in the specification or claims by reference to a particular monoclonal antibody with which it binds (e.g., CD11b, CD38), such a designation will be understood to encompass that marker even if different monoclonal antibodies are used in the identification. Phenotypic markers of interest include general markers for various subset cell types including CD3 for total T cells, CD4 for T helper/inducer cells, CD8 for T suppressor/ cytotoxic cells, and CD16/56 for NK cells; CD8-expressing subset markers such as CD11b for T suppressor cells, CD38 for activated T suppressor/cytotoxic cells, HLA-DR for activated T suppressor/cytotoxic cells, and CD57; and CD4 expressing markers such as CD25 and HLA-DR for activated T helper/inducer cells.

Of particular interest in diagnosing CFS is the evaluation of CD8+ cells, particularly for a percentage increase in the subsets of cells exhibiting activation antigens CD38 and HLA-DR as well as for a decrease in the percentage of CD11b+ cells (or a corresponding increase in CD11b– cells). While it is anticipated that further studies using additional monoclonal antibodies against other lymphocyte antigens may reveal additional markers, such additional markers (if found) will not detract from the present assay. Thus a diagnosis of CFS can be made by evaluating PMC cells for the markers discussed in this paragraph and determining whether one or more statistically different values exist in a given patient (compared to the corresponding values for the general population). A definitive diagnosis is made by determining a statistical difference in at least two of the indicated three values.

The invention also contemplates a kit for diagnosis of chronic fatigue syndrome comprising a plurality of component monoclonal antibodies or other specific binding molecules, where each of the component antibodies is specific for one of the cell markers CD11b, CD38, or HLA-DR. The antibodies are packaged together in a single container or in a plurality of individual containers for ease of use in the diagnostic assay described above. The antibodies can be bound to a solid support or be provided in a form suitable for preparation of antibody-containing solutions. The kit will normally also contain an antibody specific for the CD8 antigen. Preparation of diagnostic kits for the determination of specific antibody binding is well known in the art and need not be described here in detail. The novelty of this aspect of the invention lies not in preparation per se of the kit but in the selection of the specific antibodies. Prior to the present invention there has been no purpose for packaging together the antibodies or other binding molecules of the specificities described here.

Normal detectable labels can be used for the individual antibody components, such as fluorochromes. When a kit of the invention is designed for concurrent use of the antibodies, as occurs in fluorescent cell sorting, each of the component antibodies is labelled so as to be separately identifiable (e.g., with a fluorochrome that fluoresces at a different wavelength).

Methods for identifying and subsequently propagating relatively large amounts of the causative agent include in vitro tissue culture assays using cells susceptible to infection by the agent are also provided by the invention. Cultures comprising the infectious agent may be obtained by co-cultivating a human or animal cell culture or cell line with PMC of a CFS patient. Generally the source of infectious agent is a fluid which has been in contact with a cell from a host having been preliminarily diagnosed as having CFS, which fluid is capable of inducing CFS-associated changes such as in markers or subset populations in cultured, normal PMC cells. The cultured cells find use as a source of infectious agent (isolate) which may be used directly as a source of genomic material for preparing probes for diagnosis, antigens and vaccines, and for post-therapeutic and diagnostic purposes. Agent-specific cells which can be used to culture the CSF agent include PMC cells and selected subsets, particularly NK cells, macrophages, B cells and CD8+ cells. Various cell lines can also be used, including human cell lines such as a T cell line (for example SUP-T, MT-4), monocyte cell lines (for example U937), B cell lines (for example RAMOS, Raji), fibroblastoid cells (HOS for example), human skin fibroblasts, and neuroblastoma cells (for example SK-N-Mc). Animal cell lines which find use include 3T3 (mouse), DHK (hamster), chicken embyro, mink lung, bat lung, NRK (rat kidney), and VERO (monkey).

The general procedures for infecting and culturing the cells with the infectious agent are as follows. A cultured cell or cell line is placed in contact with a source of agent which is capable of inducing CSF associated changes in cultured PMC cells, particularly increasing the percentage of CD8+ cells expressing CD38+ or HLA-DR+. The source can be a fluid obtained directly from a host having symptoms of CFS, such as a bodily fluid, particularly whole blood, serum, saliva, and cerebrospinal fluid. Bodily fluid from an animal inoculated with any of the foregoing materials, as well as culture fluids (conditioned medium) from for example, cultures of PMC cells obtained from a CSF host may also be used.

Viral infection of the cells is followed by monitoring for a virus-related cell change over time. Virus infection generally is characterized by the appearance of virus-specific antigens, so the viral infection is properly followed by immunological methods known to those skilled in the art (for example, IFA) for detecting antigens. In addition, detection may be accomplished by microscopic observation of cytopathological changes in the inoculated cells, such as the cell ballooning and degeneration observed in RAMOS B cells after culture with PMC supernatant from CFS patients.

After viral infection and propagation, the virus can be isolated, if desired, by conventional means for releasing and purifying virus particles from cells. For example, virus particles may be isolated by lysing the cells and subjecting the lysate to standard techniques for fractionating samples containing viruses. Where possible, techniques that might disrupt virus particles should be avoided. The isolated particles will reproduce the virus-related cell change when cells are exposed to virus particles.

It may be desirable for a variety of reasons to further purify the particles present in a sample containing particles of the invention. For example, if a virus particle is to be treated and employed as a vaccine or in an immunoassay, there ordinarily should be as little in the way of extraneous protein contamination as possible. Thus, the particle should be substantially free of host proteins.

CFS viral antigens may be obtained from a variety of sources. The antigen may be present on an intact virus particle, a partially degraded virus particle, a protein- or carbohydrate-containing molecule in solution, or any other physical form, including an antigen that has been combined either chemically or physically with a particle or solid surface, such as by attaching antigens to the surface of a test tube or to suspended particles, such as red blood cells or latex particles. An antigen of the invention is defined as a substance containing at least one epitopic site of a virus particle.

To obtain CFS viral antigens, the antigens, whether soluble or in some other form, are typically first separated from cellular contaminants, such as animal cells, cell debris, and cellular microorganisms such as bacteria. This gross separation is generally accomplished by centrifugation or by filtration using standard techniques. Ordinary filters having an average pore diameter of 0.45µ are useful in retaining gross contamination and passing through the antigens.

Additionally, antigens of the invention may be separated from undesired water-soluble materials after gross contamination is removed. Where it is desired to recover either intact virus particles or their water-insoluble fragments, it is convenient to simply remove all water soluble constituents from the sample. Suitable techniques include ultrafiltration through a membrane, use of selective flocculating or protein-precipitating agents (such as polyethylene glycol and ammonite sulfate), and chromatography. Chromatography is the most versatile method since it can be readily scaled up for commercial manufacture of antigen. Gel chromatography systems using cross-linked dextran beads are typical of the materials used. A column of a suitable gel can be selected which will permit diffusion of proteins and low molecular weight substances into the void volume of the gel beads, thereby retarding the progress of these contaminants through the column, while allowing whole virus particles to pass through virtually unimpeded. When a particular antigen is desired, other gel sizes can be selected to provide for isolation of an antigen of any particular size. The gel which is selected will thus be a matter of routine experimentation.

Any of the techniques described herein can be combined as desired. For example, isolation of particles on a cesium chloride or sucrose density gradient can be followed by disruption of particles using any of a variety of techniques and isolation of a viral antigen on gel electrophoresis, selecting for proteins binding to antibodies, e.g., antisera, specific for CFS antigens.

One technique that is particularly suitable for isolating soluble protein antigens or particle fragments is affinity chromatography. Antibodies capable of binding antigens of the invention are covalently linked or adsorbed to an insoluble support using conventional procedures. The insolubilized antibody is laced in a column. A sample containing antigen is passed through the column, where it binds to the insolubilized antibody. The immunologically-bound antigen is washed with buffer and can then be released by, for example, changing the ionic strength or pH of the wash buffer. Generally, an acidic pH is effective for releasing the bound antigen. The technique is highly effective in separating closely related proteins from the antigens of the invention.

Antigens of the invention can be used as a vaccine. A preferred starting material for preparation of a vaccine is the particle antigens produced by tissue culture of the infectious virus. The antigens are preferably initially recovered as intact particles as described above. However, it is also possible to prepare a suitable vaccine from particles isolated from other sources or non-particle recombinant antigens. When non-particle antigens are used (typically soluble antigens), proteins native to the viral envelope are preferred for use in preparing vaccines. These proteins can be purified by affinity chromatography, also described above.

If the purified protein is not immunogenic per se, it can be bound to a carrier to make the protein immunogenic. Carriers include bovine serum albumin, keyhole limpet cyanin and the like. It is desirable, but not necessary to purify antigens to be substantially free of human protein. However, it is more important that the antigens be free of proteins, viruses, and other substances not of human origin that may have been introduced by way of, or contamination of, the nutrient medium, cell lines, tissues, or pathological fluids from which the virus is cultured or obtained.

Vaccination can be conducted in conventional fashion. For example, the antigen, whether a viral particle or a protein, can be used in a suitable diluent such as water, saline, buffered salines, complete or incomplete adjuvants, and the like. The immunogen is administered using standard techniques for antibody induction, such as by subcutaneous administration of physiologically compatible sterile solutions containing inactivated or attenuated virus particles or antigens. An immune response producing amount of virus particles is typically administered per vaccinizing injection, usually in a volume of one milliliter or less.

In addition to being used in vaccines, the compositions can be used to prepare antibodies to CFS virus particles. The antibodies can be utilized directly as antiviral agents. To prepare antibodies, a host animal is immunized using the virus particles or, as appropriate, non-particle antigens native to the virus particle are bound to a carrier as described above for vaccines. The host serum or plasma is collected following an appropriate time interval to provide a composition comprising antibodies reactive with the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs.

The antibody compositions can be made even more compatible with the host system by minimizing potential adverse immune system responses. This is accomplished by removing all or a portion of the Fc portion of a foreign species antibody or using an antibody of the same species as the host animal, for example, the use of antibodies from human/human hybridomas (see below).

The antibodies can also be used as a means of enhancing the immune response since antibody-virus complexes are recognized by macrophages. The antibodies can be administered in amounts similar to those used for other therapeutic administrations of antibody. For example, pooled gamma globulin is administered at 0.02–0.1 ml/lb body weight during the early incubation of other viral diseases such as rabies, measles and hepatitis B to interfere with viral entry into cells. Thus, antibodies reactive with the CFS virus particle can be passively administered alone or in conjunction with another anti-viral agent to a host infected with a CFS virus to enhance the immune response and/or the effectiveness of an antiviral drug.

Alternatively, anti-CFS-virus antibodies can be induced by administering anti-idiotype antibodies as immunogen. Conveniently, a purified anti-CFS-virus antibody preparation prepared as described above is used to induce anti-idiotype antibody in a host animal. The composition is administered to the host animal in a suitable diluent. Following administration, usually repeated administration, the host produces antiidiotype antibody. To eliminate an immunogenic response to the Fc region, antibodies produced by the same species as the host animal can be used or the Fc region of the administered antibodies can be removed. Following induction of anti-idiotype antibody in the host animal, serum or plasma is removed to provide an antibody composition. The composition can be purified as described above for anti-CFS-virus antibodies, or by affinity chromatography using anti-CFS-virus antibodies bound to the affinity matrix. The antiidiotype antibodies produced are specific for CFS-virus particles.

When used as a means of inducing anti-CFS-virus antibodies in a patient, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable. The induction of anti-CFS-virus antibodies can alleviate problems which may be caused by passive administration of anti-CFS-virus antibodies, such as an adverse immune response, and those associated with administration of blood products, such as infection.

In addition to therapeutic uses, the particles and antigens of the invention, as well as the genetic material, can be used in diagnostic assays. Methods for detecting the presence of CFS comprise analyzing a biological sample such as a blood or CFS sample for the presence of an analyte associated with CFS virus. The analyte can be a nucleotide sequence which hybridizes with a probe comprising a sequence of at least about 16 consecutive nucleotides, usually 30 to 200 nucleotides, up to substantially the full sequence of a cDNA sequence. The analyte can be RNA or cDNA.

The analyte can be a virus particle having at least one of the following characteristics: obtainable from cells susceptible to infection with CFS, including cells from CFS patients; capable of inducing expression of virus-specific surface antigen in a cell susceptible to infection by the particle, the surface antigen being recognized by serum from a host infected with CFS and not by serum from a non-infected host; and capable of inducing cytopathological changes in exposed immune cells, such as ballooning and degeneration of RAMOS cells. The analyte can comprise an antibody which recognizes an antigen, such as a cell surface viral antigen or a CFS virus particle. The analyte can also be a CFS viral antigen.

In order to detect an analyte, where the analyte hybridizes to a probe the probe may contain a detectable label. Likewise, where the analyte is an antibody or an antigen, either a labelled antigen or antibody, respectively, can be used to bind to the analyte to form an immunological complex, which can then be detected by means of the label.

Typically, methods for detecting analytes such as surface antigens and/or whole particles are based on immunoassays. Immunoassays can be conducted either to determine the presence of antibodies in the host that have arisen from infection by CFS virus or by assays that directly determine the presence of virus particles or antigens. Such techniques are well known and need not be described here in detail. Examples include both heterogeneous and homogeneous immunoassay techniques and are based on the formation of an immunological complex between the virus particle or its antigen and a corresponding specific antibody. Heterogeneous assays for viral antigens typically use a specific monoclonal or polyclonal antibody bound to a solid surface. Sandwich assays are becoming increasingly popular. Homogeneous assays, which are carried out in solution without the presence of a solid phase, can also be used, for example by determining the difference in enzyme activity brought on by binding of free antibody to an enzyme-antigen conjugate.

When assaying for the presence of antibodies induced by CFS viruses, the viruses and antigens of the invention can be used as specific binding agents to detect either IgG or IgM antibodies. Since IgM antibodies are typically the first antibodies that appear during the course of an infection, when Ig synthesis may not yet have been initiated, specifically distinguishing between IgM and IgG antibodies present in the blood stream of a host will enable a physician or other investigator to determine whether the infection is recent or chronic. This information can then be used in conjunction with the immunological profile, particularly where the immunological profile is abnormal but not significantly different from normal. For example, if only IgM antibodies are present, it may be useful to reevaluate the host at 3-month intervals.

The genetic material of the invention can itself be used in numerous assays as probes for genetic material present in naturally occurring infections. It may be amplified as necessary. One method for amplification of target nucleic acids, for later analysis by hybridization assays, is known as the polymerase chain reaction or PCR technique. The PCR technique can be applied to detecting virus particles of the invention in suspected pathological samples using oligonucleotide primers. The PCR method is described in a number of publications, including Saiki et al., *Science* (1985) 230:1350–1354; Saiki et al., *Nature* (1986) 324:163–166; and Scharf et al., *Science* (1986) 233:1076–1078. Also see U.S. Pat. Nos. 4,683,194; 4,683,195; and 4,683,202.

For both in vivo use of antibodies to CFS-virus particles and proteins and anti-idiotype antibodies and diagnostic use, it may be preferable to use monoclonal antibodies. Monoclonal anti-virus particles antibodies or anti-idiotype antibodies can be produced as follows. The spleen or lymphocytes from an immunized animal are removed and immortalized or used to prepare hybridomas by methods known to those skilled in the art. To produce a human-human hybridoma, a human lymphocyte donor is selected. A donor known to be infected with a CFS virus (where infection has been shown for example by the presence of anti-virus antibodies in the blood or by virus culture) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies.

Antibodies secreted by the immortalized cells are screened to determine the clones that secrete antibodies of the desired specificity. For monoclonal anti-virus particle antibodies, the antibodies must bind to CFS virus particles. For monoclonal antiidiotype antibodies, the antibodies must bind to anti-virus particle antibodies. Cells producing antibodies of the desired specificity are selected.

The following examples are offered by way of illustration and not by limitation.

EXAMPLE 1

Immunologic Profile of Patients With CFS Subjects

A total of 147 consecutive patients (30 males and 117 females, age range 15–80, median age 38) who were presented for evaluation as having CFS were studied from September 1989 to November 1990. As determined either at the time of evaluation or by past medical history, their illness had been present for 1–3 years. All patients met the criteria for CFS as defined by the CDC (Kruesi M., *J. Clin. Psychiatry* (1989), 50(2):53–6) and in Table I below.

TABLE I

| | Symptoms of Patients with CFS | | |
|---|---|---|---|
| Symptoms | Group 1[b] (n = 67) | Group 2[c] (n = 21) | Total CFS Patients (n = 47) |
| Exhaustion/Fatigue | 100[a] | 5 | 70 |
| Post exertional weakness | 100 | 24 | 92 |
| Muscle Weakness | 96 | 0 | 56 |
| Severe Cognitive Dysfunction[d] | 92 | 0 | 74 |
| Abdominal/Gastro- | 90 | 0 | 84 |

TABLE I-continued

Symptoms of Patients with CFS

| Symptoms | Group 1[b] (n = 67) | Group 2[c] (n = 21) | Total CFS Patients (n = 47) |
|---|---|---|---|
| intestinal Distress | | | |
| Nausea | 89 | 0 | 46 |
| Neuroirritability | 89 | 5 | 69 |
| Sleep Disorder[e] | 89 | 0 | 58 |
| Twitching/Myoclonus | 89 | 10 | 56 |
| Frequent Headache | 81 | 14 | 59 |
| Balance problems | 75 | 5 | 66 |
| Depression[f] | 73 | 0 | 46 |
| Chills | 55 | 0 | 33 |
| Sore throat | 33 | 5 | 20 |
| Lymph Node Pain | 30 | 0 | 19 |

[a]Figures give percent of patients exhibiting symptoms.
[b]Patients in this group have 25% or less normal physical activity and major CFS symptoms.
[c]Patients in this group have 75% or more normal physical activity and mild CFS symptoms. They had marked improvement for at least 2 months in their clinical condition at the time of study.
[d]Short term memory loss, encoding, stimulus recognition.
[e]Hypersomnia and hyposomnia.
[f]In the majority of cases, the onset of depression occurred 6 months after the onset of the illness.

Control subjects consisted of healthy individuals (n=50) living in San Francisco and working at the UCSF Medical Center and subjects (n=30) seeking medical attention for clinical conditions other than CFS. The majority of these other individuals were being seen for routine physical examinations. Immunophenotypic data on these two control groups were not significantly different, so they were combined for the study as one control group (30 males, 50 females, age range 20–55, median age 32). Additional control populations evaluated and spouses and family members of CSF patients (n=11); medical personnel in contact with CFS patients (n=11); patients with acute viral-like illness (n=15); patients with systemic lupus erythematosus (SLE) (n=12) as defined by the American Rheumatology Association; patients with documented depression (n=10); and individuals with prolonged fatigue without any other clinical criteria for CFS (n=6). All non-CFS subjects were referred by physicians in the San Francisco and Chicago areas.

Blood Samples

EDTA anticoagulated blood was collected for flow cytometric studies, white blood cell counts, and differential counts. An additional serum sample was obtained for viral serologic studies.

Viral Serology

Quantitative serology was done to measure the levels of antibodies to various viruses in randomly selected sera from 40 healthy laboratory personnel controls compared to those obtained with 63 CFS patients representing 23 individuals in group 1 and 27 individuals in group 2 (as defined in Table I). The viral agents evaluated included those proposed as "candidate" agents for CFS as well as other viruses. Antibody to Adenovirus, Coxsackie B4, human herpes virus 6 (HHV6), human T cell leukemia virus I/II (HTLV-I/II), human immunodeficiency virus (HIV), rubeola, and papovavirus were assayed by indirect immunofluorescence (Lennette, *J. Clin Microbiol.* (1987) 25:199–200); antibody response to cytomegalovirus was evaluated by immune adherence hemagglutination (CMV) Lennette, *J. Clin.* *Microbiol.* (1978) 7:282–85); and Epstein-Barr virus (EBV) early antigen (EA), viral capsid antigen (VCA) and nuclear antigen (EBNA) were measured by both indirect immunofluorescence and anti-complement indirect immunofluorescence (Reedman, *Int. J. Cancer* (1973) 11:499–520; and Lennette (1987) supra).

Sample Preparation and Flow Cytometric Analysis

Lymphocyte and monocyte populations were analyzed by flow cytometry using dual color direct immunofluorescence after whole blood lysis (Coon et al., *Lab. Invest* (1987) 57:453–79). The panels of fluorescein isothiocyanate (FITC) or phycoerythrin (PE) monoclonal antibodies used are listed in Table II below. A single laser flow cytometer (FACScan™): Becton Dickinson Immunocytometry Systems, San Jose, Calif.) which has the capability of discriminating forward and side scatter as well as two fluorochromes was used with the Consort 30 software.

TABLE II

Immunophenotyping Panel Used for Evaluation of CFS Patients

| Cell Subset | Antibody Specificity |
|---|---|
| CD3 | Total T |
| CD4 | T helper/inducer (T H/I) |
| CD3CD8 | Cd8+ T suppressor/cytotoxic (T S/C) |
| CD8CD11b | Suppressor T cell |
| CD8CD28 | Cytotoxic T cell |
| CDUCD57 | T S/C Subset |
| CD8Leu8 | T S/C Subset |
| CD16CD56 | Natural killer |
| CD20 | B cell |
| CD5 CD20 | B cell subset |
| CD14 | Monocyte |
| Activation Markers | |
| CD4CD25 | Activated T H/I |
| CD4HLA-DR | Activated T H/I |
| CD8CD38 | Activated T S/C |
| CD8HLA-DR | Activated T S/C |
| CD8CD25 | Activated T S/C |
| CD16CD25 | Activated NK |
| CD16HLA-DR | Activated NK |
| CD14CD25 | Activated NK |
| Cell Adhesion Markers | |
| CD11a | Adhesion molecule integrin family (LFA1-a) |
| CD18 | Adhesion molecule integrin family 9LFA1-b) |
| CD44 | Homing receptor |
| CD54 | Intracellular adhesion molecule (ICAM-1) |

The method used was as follows. A 100 µl sample of whole blood was aliquoted into tubes, monoclonal antibody was added, and the mixture incubated for 15 minutes at room temperature. Red cells were lysed with a commercial lysing reagent (FACsLyse™) for 10 minutes, and the lysate spun down and washed with phosphate buffered saline (PBS) containing 3% fetal calf serum and 0.1% sodium azide. The white cells were resuspended in the wash buffer and fixed with a final concentration of 1% paraformaldehyde. Lymphocyte gates were confirmed by the HLE FITC (CD45), LeuM3 PE (CD14) antibody combination (Leukegate). Evaluation of the cell adhesion antigens on lymphocyte, monocyte, and neutrophil populations was performed using indirect immunofluorescence staining.

Data Analysis and Statistics

The Mann-Whitney U and Kruskall-Wallis tests were used to evaluate difference in immunologic markers between the groups of patients, since these markers are known to have non-Gaussian distribution (Siegel, (1956) McGraw Hill Book Co., New York). Student's T-test for independent samples or one-way analysis of variance (SPSS-PC+ Release 4.0, SPSS, Inc., Chicago) was used to evaluate differences between the groups for other continuous variables. When more than 2 groups were evaluated, the Scheffe' test was employed to identify the groups for which the differences were significant.

Clinical Evaluation of CFS Patients

The individuals referred with the suggested diagnosis of CFS were evaluated for a large number of symptoms (Table I), past medical history and physical findings. A full report on the clinical aspects of their illness will be the subject of another publication. All the patients had a past history of fatigue for more than six months, post exertional weakness substantially worse than previously observed in the past, muscle weakness, myalgias and frequent headaches. Many had gastrointestinal symptoms with nausea, and neurologic findings that include sleep disorders, severe cognitive dysfunction, neuroirritability, myoclonus and balance problems (Table I). About 50% gave a medical history of flu-like illness at the onset of this clinical condition. Only 8 patients had depression prior to the onset of the illness, but many (80%) developed depression after 2 years of illness. Based on their symptomatology, the CFS patients could be placed into three groups: Group 1 consisted of 67 patients whose illness was so severe that they had less than 25% of their normal daily activity and multiple symptoms, Group 2 consisted of 21 patients who initially had severe symptoms and incapacitating illness like Group 1; however, at the time of evaluation they had made substantial improvement for at least 2 months and regained 75% or ore of their normal physical activity with only mild symptoms; 59 individuals with reduced physical activity continued to have moderate symptoms. Healthy controls had none of the symptoms listed in Table I on a persistent basis.

Viral Serology

The prevalence and titers of antibodies to CMV, EBV-VCA, EBNA, rubeola, adenovirus type 2, and the papovavirus (BK virus) did not differ between healthy controls and CFS patients (Table III).

TABLE III

Comparative Serosurvey of Antiviral Antibodies in CFS Patients and Control Subjects

| Virus | Healthy Controls N = 40 | | CFS Patients N = 63 | |
|---|---|---|---|---|
| | GMT[a] | (%+) | GMT | (%+) |
| Cytomegalovirus | 42 | (40) | 67 | (46) |
| Epstein-Barr | | | | |
| VCA | 314 | (95) | 393 | (95) |
| EA | 25 | (15) | 40 | (51)[b] |
| EBNA | 206 | (95) | 96 | (95) |
| Rubeola | 473 | (98) | 577 | (89) |
| HHV-6 | 104 | (98) | 201 | (100) |
| Adenovirus | 285 | ((%) | 155 | (81) |
| Coxsackie B4 | 113 | (65) | 134 | (90)[b] |
| Papovavirus BK | 83 | (55) | 61 | (44) |
| HTLV-II | | (0) | | (0) |
| HIV-1/HIV-2 | | (0) | | (0) |

[a]GMT = geometric mean titer.

TABLE III-continued

Comparative Serosurvey of Antiviral Antibodies in CFS Patients and Control Subjects

| Virus | Healthy Controls N = 40 | | CFS Patients N = 63 | |
|---|---|---|---|---|
| | GMT[a] | (%+) | GMT | (%+) |

[b]The seroprevalence is statistically significant ($p<0.001$) by Chi square analysis.

Evaluation of CFS patients based on clinical status as defined in Table I also showed no differences in these viral antibody titers as compared to controls. No antibodies to HTLV-I/II and HIV were found in any subjects. Antibody titers to HHV-6 in the CFS patients were twice as high as those found in controls, but were not significantly different ($p>0.05$). The prevalence of antibodies to Coxsackie B4 virus was significantly higher in the CFS group compared to controls (90% vs. 65%) ($p<0.001$), but the geometric mean titers were approximately the same. Moreover the prevalence of antibodies to EBV-EA was significantly different between the CFS patients and controls 51% vs. 15%) ($p<0.001$). This finding was specific for EA since the VCA and EBNA seropositivity rates for both groups were identical.

Peripheral white Blood Cell Analyses: Lymphocyte nd Monocyte Phenotypic Profile

The total number of white blood cells ($6–10\times10^3/mm^3$) was not different between CFS patients and healthy control groups. Evaluation of the total lymphocyte, monocyte and neutrophil populations also showed no differences between control and CFS patients whether the latter were considered as total or separate groups (Table I). Cell surface phenotypic analysis of the major lymphocyte populations including T (CD3), B (CD20), and NK (CD16+/CD56+) cells indicated no significant differences between CFS patients and controls (Table IV).

TABLE IV

Peripheral Blood Phenotypic Profile in CFS and Healthy Individuals

| Surface Markers | CFS (n = 147) | Controls (n = 80) |
|---|---|---|
| % CD3+ (total T cell) | 71 ± 8[a] | 74 ± 8 |
| % CD4+ cell | 46 ± 9 | 48 ± 9 |
| (T helper/inducer cell) | | |
| CD4+ cell number | 834 ± 315 | 889 ± 273 |
| % CD8+ cell | 24 ± 8 | 22 ± 4 |
| (T suppressor/cytotoxic) | | |
| CD8+ cell number | 468 ± 227 | 488 ± 220 |
| % CD20+ cell (B cells) | 11 ± 16 | 10 ± 3 |
| % CD16/CD56+ (NK cell) | 13 ± 4 | 14 ± 8 |
| Helper/Suppressor Ratio | 1.7 ± 0.5 | 1.8 ± 0.4 |
| % CD4+ Cells Expressing | | |
| CD25 | 33 ± 7 | 34 ± 6 |
| HLA-DR | 12 ± 6 | 10 ± 7 |
| % CD16+ Cells Expressing | | |
| CD25 | 4 ± 1 | 3 ± 2 |
| HLA-DR | 3 ± 1 | 3 ± 1 |
| % CD14+ Cells Expressing | | |
| CD25 | >1 | >1 |

[a]Data represent mean ± standard deviation.

Evaluation of the percentage and absolute number of CD4+ and CD8+ T cells also demonstrated no significant differences (p>0.05) from the controls (Table IV). Analysis of the CD4:CD8 ratios of cells in our patient population showed 88% had ratios within our normal range (1–2.5), 5% had decreased CD8+ cells and 7 had increased CD8+ cells (ratio<1.0). Taken together the average CD4/CD8 ratio for all CFS patients (1.7+0.5) did not differ significantly from controls (1.8+0.4) (p>0.05).

Analysis of activation antigens (CD25 and HLA-DR) on CD4+ T cells, NK cells or monocytes showed no significant differences in CFS patients from healthy controls. Analysis of a B cell subset (CD5/CD20) that has been found to be elevated in autoimmune disease (Casali et al., Science (1987), 236:77–81) also indicated no differences between CFS and healthy controls. In addition, flow cytometric studies of the cell adhesion antigens (CD11a, CD18, CD44, CD54) showed no differences in percentage positive or the fluorescence intensity of cells obtained from CFS patients compared to healthy controls.

CD8 Cell Subset Analysis

Previous cell surface marker studies in documented acute viral infections such as EBV, CMV, and HIV infection, have shown elevation of CD8+ cells which express activation antigens (CD38, HLA-DR) (Carney et al., J. Immunol., 1981, 126:2114–16; Tomkinson et al., J. Immunol., 1987, 139:3802–07 and Landay et al., Sixth International Conference on AIDS, San Francisco, Calif., 1990, p. 141). In the case of the herpes viruses, these cell numbers return to normal 2 to 4 weeks following infection. We evaluated a number of cell surface antigens expressed on CD8+ T cells from the 147 CFS patients and compared them to the 80 healthy controls (FIG. 1). In addition, the results with the two separate clinical subgroups (Table I) were considered.

Three markers gave noteworthy results. With the total CFS patients, the population of CD8+ cells expressing CD11b were somewhat decreased when compared to the normal controls (19±16 vs. 25±10) indicating a drop in the phenotypic suppressor CD8+ T cell compartment. Since the number of total CD8+ cells is not changed, a concomitant increase in the phenotypic cytotoxic (CD8+ CD28+ CD11b–) population is seen. This result was confirmed in a preliminary study showing a rise in the CD8+ CD28+ population in these patients. Evaluation of activation antigens on the CD8+ cells showed an increase in CD38 (47±20 vs 35±12 for Controls) and HLA-DR (22±8 vs 14±6 for Controls) expression. An additional activation antigen CD25, as well as the CD57 and Leu8 antigens were expressed on the CD8+ cells at a level comparable to controls.

When these same CD8+ cell subsets were considered in Group 1 patients, the differences as compared to healthy controls (FIG. 1) reached statistical significance. In contrast, evaluation of the CD8+ cell subsets among the CFS patients who improved in their clinical status (Group 2) showed no significant differences from healthy controls (FIG. 1). The 59 patients who had moderate symptoms also had CD8+ cell abnormalities, but they were not statistically significant. Further evaluation of Group 2 showed only 10% of patients had two or more significantly abnormal results among the CD8+ CD11b–, CD8+ CD38+, or CD8 +HLADR+ subsets, whereas among the Group 1 patients 85% had 2 or more abnormal results. These data indicate a high probability (90%) of having active CFS if an individual has two or more of the CD8+ cell subset alterations.

To control for possible alteration in cell surface antigens by the whole blood lysis procedure, a subset of patients was evaluated following Ficoll-Hypaque isolation of peripheral blood mononuclear cells. No differences were seen between the whole blood lysis procedure and Ficoll-Hypaque purified cells.

CD8 Cell Markers in Other Control Populations

To evaluate the specificity of the CD8+ cell alteration in CFS patients, several individuals with other clinical conditions were evaluated with the same panel of monoclonal reagents. Among patients who had an acute viral-like illness (common cold or flu-like illness), a number of observations were made. The initial cellular response demonstrated an increase in both percentage and absolute numbers of natural killer cells (CD16+/CD56+). These natural killer cells were CD8+, CD38+, CD11b+, and HLADR– as determined by multiparameter flow cytometric studies. In several of the individuals studied we noted this initial natural killer response was followed by an increase in activated CD8/CD11b T cells (CD38+ HLA-DR+). In all these subjects, recovery 1–2 weeks later was accompanied by a return to normal of all these immunologic parameters. All other CD8+ cell markers were normal in these individuals.

Evaluation of CD8+ subsets in patients with a diagnosis of depression showed no significant differences compared to healthy controls. Furthermore, family members and contacts of CFS patients demonstrated normal CD8+ subsets as well as those individuals presenting with fatigue other than CFS (Table V).

TABLE V

| | CD8+ Cell Surface Markers in Control Populations | | | | | | |
|---|---|---|---|---|---|---|---|
| CD8+ Cells Expressing | Acute Viral (n = 15) | Autoimmune Depression (n = 10) | Family Members[b] (n = 11) | Contacts[c] (n = 11) | Chronic Fatigue CF Alone (n – 6) | Autoimmune Disease (n = 12) | Healthy Controls (n – 80) |
| CD11b | 42; 12 | 28; 10 | 27; 12 | 27; 8 | 30; 12 | 28; 6 | 25; 10 |
| CD38 | 63; 10[a] | 26; 8 | 28; 7 | 32; 6 | 25; 6 | 45; 12 | 53; 12 |
| HLA-DR | 12; 3 | 10; 5 | 10; 6 | 12; 6 | 9; 3 | 15; 4 | 14; 6 |
| CD16/56 | 24; 7 | 12; 4 | 8; 2 | 11; 4 | 10; 5 | 12; 6 | 14; 8 |

[a]Statistically significant (Schiffe test) compared to healthy controls at p<0.05.
[b]Spouses or family members of CFS patients.
[c]Contacts are medical personnel coming in contact with CFS patients.

Laboratory findings among CFS patients have shown low level autoantibodies which may reflect an underlying autoimmune disease (Buchwald et al., Review Infect. Dis., 1991, 13:512–18). Evaluation of patients with SLE showed only increased expression of the CD38 marker on CD8+ cells (Table V); other cell surface markers were within the normal range.

Example 2

Isolation of Infectious Agent for CFS

1. Inoculation of Animals

One method for identifying a new agent involved in human disease is to infect a susceptible animal with putatively diseased tissue. The animals can be observed for the development of symptoms, and the agent can be detected by standard microbiological and serological methods. We use newborn NSF mice selected because of their low level endogenous virus production (Levy *Current Topics in Microbiology and Immunology* (1978) 7:111), and the sensitivity of mice to a variety of human agents (Hsiung, *Diagnostic Virology* (1982); and Prusiner, *Ann. Rev. Micro.* (1989) 43:345). Syrian hamsters are chosen for their susceptibility to several infectious agents including human parvoviruses and "prions," (Fraenkel-Conrat, *Virology* (1988); Prusiner, *Ann. Rev. Micro.* (1989) 43:345; and Berns, Plenum Press (1984)), their relative ease of study, and low cost of purchase and maintenance. After inoculation with patient material, each animal is observed for development of physical abnormalities or disease. The animals are inoculated intraperitoneally (IP) or subcutaneously (SC) with the following patient specimens:

a. 0.1–0.2 ml whole blood
  b. separated PMC ($10^{3-10^6}$ cells) in 0.2 ml

Control animals receive blood and PMC from normal, healthy donors. In addition, some hamsters receive material intracerebrally, since this approach has helped detect the presence of human parvoviruses and prions (Fraenkel-Conrat, *Virology* (1988); Prusiner, *Ann. Rev. Micro.* (1989) 43:345; and Berns, K.I. Plenum Press (1984).

All specimens are inoculated within 24 hrs. after removal from the subject. The PMC of the CFS patient are separated by Ficoll/Hypaque density gradient as is routinely conducted in the laboratory (Castro, *J. Clin. Microbiol.* (1988) 26:2371). The PMC are suspended in RPMI 1640 medium without serum for inoculation into the animals. Similar studies with small animals were conducted in the initial attempts to find the AIDS virus, (Morrow, *J. Gen. Virol.* (1987) 68:2253).

For these studies, the specimens from 10 CFS patients are injected into 100 newborn animals from each species each year. These animals are followed for any signs of disease, including neurologic abnormalities or changes in their immune responses (see below). Litter mates receive blood or PMC from 5 normal donors as controls.

2. Studies on Inoculated Animals a. The animals are followed daily for any signs of disease. A full physical examination is conducted weekly. They are evaluated for failure to thrive, ruffled fur, enlargement of the spleen or thymus, pneumonia and neurologic disorders (unsteady gait or paralysis).

b. For the first three months, control animals and those inoculated with patient material are bled once every two weeks either intraorbitally or from the tail vein. A complete blood count and differential is done. In particular, activation markers on the CD8+ cells of mice (for which markers are available) are measured (Eichmann, *Immunol Rev.* (1989) 109:39). In hamsters, the relative presence of lymphocytes, and macrophages is assessed and compared to controls. Serum is collected monthly to test for a potential agent that has hemagglutinating activity against human, chick, goose, guinea pig and sheep erythrocytes as measured by conventional techniques (White, *Medical Virology* (1986) and Hsiung, *Diagnostic Virology* (1982)). These approaches were used in the initial search for the AIDS virus. After three months, these studies are repeated every 6 weeks or when animals show signs of disease. All animals are maintained for one year.

c. Any sick animal or animal showing a change in normal immunologic profile is sacrificed and evaluated using the following protocol: tissues are examined for gross pathology and fixed for microscopic examination (see Table A). Any tissues showing abnormalities are examined by electron microscopy (EM) (see Table B). Extracts of the tissues and the blood are reinoculated into newborn animals of the same strain in an attempt to transfer the putative etiologic agent. They are also inoculated onto selected cultured animal and human cells that are examined for evidence of a pathogen such as CPE, hemadsorption, RT activity (see Table 6). With some sick animals, attempts are made to establish the animal cells, particularly PMC, in culture for further evaluation.

d. The PMC of the mouse strains separated by Ficoll/Hypaque procedures are grown in the presence of mouse T cell growth factor (Smith, *Immunol. Rev.* (1980) 51:337), which is available commercially. Human IL-2 also can be used for these procedures as well as those using separated PMC from hamsters. Supernatants from inoculated cells and cell lines are checked for reverse transcriptase activity (Mn++ and Mg++ dependent) and hemagglutinating activity (White, *Medical Virology* (1986) and Hsiung, *Diagnostic Virology* (1982). If positive, they are inoculated back into animals to assess the presence of a pathologic agent.

e. Sera from the animals, after absorption with normal human lymphocytes, is tested by immunofluorescence assays (IFA) for reactivity with PMC cultures of individuals with CFS and with cells inoculated with specimens from these animals. Any positive result may reflect growth of the agent in the animal host.

3. Tissue Culture Studies a. Whole blood, PMC, sera, saliva and cerebrospinal fluid specimens from patients with CFS are evaluated for the presence of an infectious agent by inoculation onto normal PMC cultures and a variety of cell lines (see Table VI), following pretreatment with polycations to increase their sensitivity to virus infection (Castro, *J. Clin. Microbiol.* (1988) 26:2371).

TABLE VI

| Cell Lines Used for Detection of the CFS Agent* | |
|---|---|
| Animal Cell Lines | Human Cells |
| mouse 3T3 | Sup-T - T cell line |
| BHK hamster | MT-4 - T cell line |
| chicken embryo | U937 - monocyte cell line |
| mink lung | RAMOS - B cell line |
| bat lung | Raji - B cell line |

TABLE VI-continued

Cell Lines Used for Detection of the CFS Agent*

| Animal Cell Lines | Human Cells |
|---|---|
| NRK - (rat) kidney | HOS - human fibroblastoid cells |
| Vero (monkey) | human skin fibroblast |
| | SK-N-Mc - neuroblastoma cells |

*Cell lines are routinely checked for mycoplasma contamination. These lines are selected because of their cell type and use in the laboratory for growth of known viruses.

These cells are subsequently examined for an infectious agent by the procedures listed in Table VII, including hemadsorption procedures using guinea pig and chick erythrocytes (White, *Medical Virology* (1986) and Hsiung, *Diagnostic Virology* (1982)). This latter approach was instrumental in initially finding the simian type D retrovirus (Marx, *Science* (1984) 223:1083).

TABLE VII

Procedures to be Used Routinely for Detection of an Infectious Agent in Cultures of CFS Tissues

1. Cytopathic effects (balloon degeneration, enlarged cells, syncytia)
2. Hemadsorption (cells)
3. Hemagglutination (fluid)
4. Reverse transcriptase activity ($Mg^{++}$, $Mn^{++}$) (fluid)
5. Induction of antigens in the cells (detected by IFA)

Supernatant from these cultures is passed twice to fresh cells of the same type to enhance the sensitivity for detection of the agent. Endogenous retroviruses can be expressed in some of the cell lines (e.g., mouse, rat, mink, MT-4) (Levy, *Cancer Res.* (1986) 46:5457 and Levy, *Current Topics in Microbiol. and Immunol.* (1978) 7:111) and any RT activity is assessed for its association with an endogenous virus. Specific antisera against these agents are available.

4. Isolation of an infectious agent

Our laboratory, over the past four years, has evaluated peripheral blood mononuclear cells (PMC), cerebrospinal fluid (CSF), saliva, and cervical swabs obtained from 96 patients with CFS for the presence of an infectious agent (see Table VIII).

TABLE VIII

Tissue Culture Studies to Detect Infectious Agents in Chronic Fatigue Syndrome

| Specimen | No. Tested | No. Positive# |
|---|---|---|
| PMC | 96 | 8 |
| Plasma | 24 | 1 |
| CSF | 2 | 0 |
| Saliva | 15 | 1 |
| Cervical swab | 1 | 0 |

See Table 4 for details on positive specimens.

These studies involved the culturing of the PMC with and without mitogen-stimulated normal PMC similar to approaches used to isolate the AIDS virus (Castro, et al., *J. Clin. Microbiol.* (1988) 26:2371). In addition, in some studies, the isolation of a potential agent was attempted on a variety of different animal and human cell lines (see Table VII). Thus far, evidence of a potential cytopathic agent has been noted in eight of the individuals studied (Table VIII). Cytopathology was observed in the PMC cultures of three, and in three others when fluid from the PMC culture was passed to the RAMOS B cell line (see Table IX).

TABLE IX

Detection of Infectious Agents Associated with Chronic Fatigue Syndrome

| Specimens | Cells Detected | How Detected |
|---|---|---|
| PMC | PMC | CPE |
| PMC | PMC | CPE |
| PMC | PMC | CPE |
| PMC | PMC | RT |
| PMC | PMC | RT |
| PMC | PMC | RT |
| PMC | Ramos | CPE |
| PMC | Ramos | CPE |
| PMC | Ramos | CPE |
| Saliva* | PMC | CPE |
| Plasma* | PMC | CPE |

RT - Mn++-dependent reverse transcriptase activity in the culture fluid.
CPE - cytopathic effects as demonstrated by giant cells and balloon degeneration in the cells listed (FIG. 1).
PMC - peripheral blood mononuclear cells.
*PMC of patient also gave evidence of an infectious agent.

In 1 out of 15 patients, saliva induced cytopathic changes in the PMC culture. Neither of 2 cerebrospinal fluids nor a single cervical specimen showed any CPE-inducing agent, but one out of fifteen plasma samples gave CPE in RAMOS cells. The observations with saliva were most likely due to HHV-6 as this virus has recently been found in the saliva of most individuals (Levy, et al., *The Lancet* (1990) 335:1047). None of the animal or other human cells showed evidence of any agent by morphologic or serologic criteria (e.g., IFA).

As noted above, in six PMC cultures an agent was found that led to cytopathic changes in the RAMOS B cell line. Subsequent studies using immunofluorescent techniques (conducted by E. Lennette) indicated that this CPE was associated with staining of 0.1% of the cells by CFS sera; the results did not reflect infection by EBV, HHV-6 or any other human virus considered (see Table X for list).

TABLE X

Antibodies to Human Viruses in CFS Patients and Controls

| | CFS | | Control | |
|---|---|---|---|---|
| Viral Agent | | Positive | | Positive |
| Adenovirus type 2 | N = 64 | 19 (30%) | N = 10 | 5 (50%) |
| Coxsackie B4 | N = 64 | 35 (55%) | N = 10 | 6 (60%) |
| N = 64 | | | | |
| CMV | N = 92 | 45 (49%) | N = 10 | 5 (50%) |
| Measles | N = 28 | 26 (89%) | N = 28 | 26 (92%) |
| EBV | N = 64 | 63 (89%) | N = 10 | 9 (90%) |
| HHV-6 | N = 52 | 51 (98%) | N = 59 | 58 (99%) |
| HIV | N = 96 | 0 (0%) | N = 59 | 0 (0%) |
| HTLV-I/II | N = 64 | 0 (0%) | N = 10 | 0 (0%) |

Subsequent passage of supernatant from the cultures to fresh RAMOS cells did not lead to the isolation of an infectious agent. The induction of CPE and antigen was achieved for 2-3 passages and then these cell culture observations were no longer observed. In the final cultures in which the virus was not noted, attempts to activate the agent with halogenated pyrimidines (e.g., IUDR) also did not recover a CPE-inducing agent.

The fluid from one PMC culture induced cytopathic changes leading to cell death in macrophage cultures from normal controls (Table VIII). Passage of this filterable CPE-producing agent in the supernatant was achieved for 2 passages and then lost as was our experience with the RAMOS cell agents described above.

Finally, in 31 PMC cultures evaluated for reverse transcriptase (RT) activity (Hoffman, et al., *Virology* (1985) 147:326), 3 cultures gave levels >10,000 cpm/ml of culture supernatant using $Mn^{++}$ as the cation. No RT activity with $Mg^{++}$ was noted. For these studies, we routinely used frozen and thawed cell pellets to detect any cell-associated viruses as is the case with HTLV-1 (Fraenkel-Conrat, et al., *Virology* 2nd Ed. (1988); and Levy, *Cancer Res.* (1986) 46:5457). However passage of the RT activity to fresh cultures did not lead to induction of RT activity nor isolation of a retrovirus. We have presumed the initial RT activity reflected cellular polymerases.

b. PMC from CFS patients is cultured in RPMI 1640 medium with and without IL-2, with and without PHA, and cocultivated with PMC from normal donors (obtained from Irwin Memorial Blood Bank, San Francisco) or the Ramos cell line. (Castro, *J. Clin. Microbiol.* (1988) 26:2371). These approaches permit relative preferential growth of white cell subsets that may or may not yield the CFS agent. (Castro, *J. Clin. Microbiol.* (1988) 26:2371). The Ramos line is used because of its previous signs of CPE after inoculation with PMC cell fluid from a CFS patient (see FIG. 1). These cultures are examined for CPE and RT activity, and other signs of an infectious agent (see Table 6) including induction of antigens detected by IFA using the patient's serum. Fluid is also inoculated onto selected animal and human cell lines (see Table VI) for further evaluation of a replicating agent (see FIG. 2 for summary of this approach).

c. Sera from individual patients is used to examine the cells by IFA for a potential infectious agent.

d. Sera from individual patients is also examined for the presence of an infectious agent by measuring hemagglutinating activity using conventional assays with sheep, chick, guinea pig, and human erythrocytes (White, *Medical Virology* (1986)).

e. Culture of Purified subsets of peripheral white cells obtained from CFS patients 1) Attempts will be made to identify the CFS infectious agent in culture by techniques developed for efficient isolation of the AIDS virus. In particular, selective culture of CD8+, CD4+, T-cells, B-cells, macrophages and NK cells is conducted to examine the possible presence of the CFS agent in one of these cell types. The cells are cultured selectively since one cell type may prevent replication of the agent in another cell type. For example, removal of CD8+ cells from some PMC cultures has enabled recovery of HIV from the cells when the virus could not be detected otherwise (Walker, *Science* (1986) 234:1563 and *Immunology* (1989) 66:628).

The cell selection and depletion is undertaken using immunomagnetic (IM) beads (Gaudemack, et al., *J. Immunological Methods* (1986) 90:179). The PMC are isolated from each sample using monoclonal antibody-coated beads (Dynabeads, M-450 Dynal, Oslo, Norway) with selectivity for the major human cell subsets. Twenty to fifty million PMC are suspended in 4–5 ml of phosphate buffered saline (PBS) containing 2% heat-inactivated (30 min., 56° C.) fetal calf serum (FCS). This single cell suspension is added to the IM beads (previously washed 3 times with cold PBS containing 2% FCS) to yield a bead:target cell ratio of approximately 3:1. The bead cell suspension is incubated at 4° C. on a rotating rocking machine for 30–35 min. Cells rosetting with IM beads are captured by placing the tube in a magnetic device (Dyno magnetic particle concentrator) for 1–2 min. followed by removal of the supernatant containing the non-bound cells. The rosetted cells are washed 3 times with cold PBS containing 2% FCS using the magnetic capture device noted above and then counted. The non-adherent cells are subsequently treated with other IM beads coated with a different monoclonal antibody and the procedure repeated.

This approach with IM beads can also be performed by first reacting the PMC with mouse monoclonal antibodies to specific cell surface markers. Then, beads with antibodies to mouse immunoglobins are added to select or deplete a specific cell type. The purity of the subset is analyzed by double-staining procedures on a Becton-Dickinson FACscan using specific monoclonal antibodies (Levy, et al., *Clin. Immunol. Immunopathol.*, (1985) 35:328).

2). All cells obtained from the blood are cultured in the presence of IL-2 (Pharmacia, Silver Spring, Md.) except for macrophages. They are grown in 10% FCS and 5% human (AB+) serum as described in Homsy, et al., *Science*, (1989) 244:1357. The cells are examined for modulation of cell surface markers by FACS analysis (see below) and for morphologic changes. The cells and fluids are monitored for an infectious agent every 3 days, for up to 28 days by the procedures listed in Appendix 6. This period of time has been found necessary for detection of HIV in the cells of some infected individuals (Castro, et al., *J. Clin. Microbiol.*, (1985) 26:2371). The cells are activated with PHA, pokeweed mitogen (PWM), or another mitogen specific for each cell type. Supernatants from the cultures are obtained and passed to fresh cells from normal controls.

Included in these studies is the cultivation of the different cells or their fluids with established human T, B, and macrophage cell lines, and animal cell lines (see Appendix 3). Induction of CPE, RT activity, or specific IFA staining would be used to detect infection. Finally, to augment detection of an agent, halogenated pyrimidines (e.g., IUDR) to activate virus replication are used.

f. Specific Studies of Macrophages

In the initial studies (see Preliminary Studies, Section C) CPE in normal macrophages inoculated with supernatant fluid from the PMC culture of an individual with CFS was found. To rule out a cytokine effect, filtered material from these cultures was then passed to fresh macrophages and CPE was again noted as demonstrated by cell death and granular formation in the cells. However, continued passage of this CPE-inducing effect was not achieved.

These studies are being repeated using macrophages of CFS patients as a source of supernatant fluid. They are obtained by adherence to plastic as described in Homsy, et al., *Science*, (1989) 244:1357. Trypsinization is used to maintain purity of the cells. Cells are followed for the presence of an infectious agent as described (see Appendix 6). In addition, fluids from the macrophages as well as CDS+, CD4+, B cells and NK cells from CFS patients are inoculated onto macrophages from control individuals to evaluate whether there is a transferable morphologic effect on these cells in culture.

The culture supernatants from CFS macrophages are also inoculated onto a selection of animal and human cells (see Appendix 3) and their possible induction of CPE, RT activity, and antigen is evaluated as noted above.

g. Specific Studies with NK Cells

A common finding in CFS is decreased NK cell function (Kibler, et al., *J. Clin. Immunol.* (1985) 5:46; Murdoch, *NZ Med J* (1986) 1015511; Caligiuri, et al., *J. Immunol* (1987) 139 (10):3306; Klimas, et al., *J. Clin. Micro.* (1990) 28(6):1403). Therefore, a patient's NK cells purified by CD16/CD56 IM beads, or the cell culture fluid is cocultured with normal NK cells to transfer an infectious agent detected as described (see Table 6). These normal NK cells are assessed for function by measuring their ability to kill $^{51}$CR-labelled K562 cells (Baron, et al., *Diagn. Immunol.* (1985) 3:197; Hudson, et al., *Practical Immunology*, 2nd Ed. Blackwell Scientific Publications, Oxford (1980), (see Section C)).

h. Specific Studies with CD8+ Cells

We have found that the CD11b+ cells (suppressor CD8+ cells) decrease during CFS. We plan to select for the CD8+/CD11b+ cells with IM beads and examine them for a possible infectious agent. The procedures are similar to those described above for NK cells. In addition, supernatant from the CD11b+ cells is removed and added to CD11b+ cells of normal donors to see if any cytopathic effects are noted that could explain the reduction in this particular cell subset. An effect on expression of cell surface markers is measured by FACS analysis. Cells are monitored for an infectious agent as described in Table 6. In addition, an effect of the cell supernatant from CD11b+ cells on mitogen-induced proliferation of normal lymphocytes and their production of gamma interferon is evaluated (Klimas, et al., *J. Clin. Micro.* (1990) 28(6):1403; Hudson, et al., *Practical Immunology*, 2nd Ed. Blackwell Scientific Publications, Oxford (1980). (see Section C)).

4. PCR Analysis

To evaluate whether an occult retrovirus might be the cause of CFS, PCR analysis is performed on PMC specimens from CFS patients and controls with gag and polymerase probes of HTLV-1, HTLV-II and HIV. In brief; $2\times10^6$ cells are extracted and the PCR performed on the DNA as described in Ou, C—Y, et al., *Science* (1988) 239:295, Innis, PCR Protocols, *Academic Press* (1990). Two separate gag specific primer base pairs for HIV are used: SK38/39 and SK101/145. A set of gag primers, SG166/SK296, and a set of pol primers, SK110/111, for HTLV-I is used. The Cetus thermocycler is used for 30 cycles each for 30 sec at 95°, 55° and 72° C. respectively. The amplified product is hybridized to oligomer probes for HIV-1 (SK19 and SK102) and probes to HTLV-I gag (SG242) and pol (SK112, 1SK18). The resulting products are analyzed by polyacrylamide gel electrophoresis and autoradiography.

Similar PCR evaluation is performed using DNA probes characteristic for other viral families such as parvoviruses, herpes viruses, papilloma viruses, and enteroviruses.

All publications and patent applications cited in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for aiding in the diagnosis of chronic fatigue syndrome (CFS), comprising the steps of:

(a) obtaining a sample of peripheral mononuclear cells from a host;

(b) contacting the sample with an immunophenotypic panel comprising monoclonal antibodies for CD8$^+$ antigens, CD11b antigens, CD38 antigens and HLA-DR antigens; and (c) allowing the antibodies to bind to an antigen and classifying said host as having CFS when said sample shows at least two of the following conditions:

(i) a reduction in the percentage of CD8$^+$ CD11b+ cells; or (ii) an increase in the percentage of CD8$^+$ CD38+ cells, or (iii) an increase in the percentage of CD8$^+$ HLA-DR cells as compared to percentages of cells having said markers obtained using control hosts not having chronic fatigue syndrome.

2. The method of claim 1, wherein binding of antibodies to said cells is measured by detecting the presence of a fluorochrome attached to said antibodies.

3. The method of claim 1, wherein evaluating said sample for CD11b cells further comprises determining an increase in the number of CD11b− cells.

4. The method of claim 1, wherein said peripheral mononuclear cells are obtained from a blood sample from said host.

5. A kit for aiding in the diagnosis of chronic fatigue syndrome, comprising:

an immunophenotypic panel of antibodies which includes monoclonal antibodies for CD8+ antigens, CD11b antigens, CD38 antigens and HLA-DR antigens, wherein each of the antibodies of the panel is labelled so as to be separately identifiable when used concurrently.

* * * * *